US012201541B2

(12) United States Patent
Bagaoisan et al.

(10) Patent No.: US 12,201,541 B2
(45) Date of Patent: Jan. 21, 2025

(54) VASCULAR ACCESS DEVICES AND METHODS FOR LOWER LIMB INTERVENTIONS (71) Applicant: RAM MEDICAL INNOVATIONS LLC, Springfield, OH (US)

(72) Inventors: Celso Bagaoisan, Union City, CA (US); Suresh Pai, Los Altos, CA (US); Azim Shaikh, Beavercreek, OH (US); Mubin I. Syed, Springfield, OH (US)

(73) Assignee: RAM MEDICAL INNOVATIONS, INC., Springfield, OH (US)

( * ) Notice: Subject to any disclaimer, the term of this patent is extended or adjusted under 35 U.S.C. 154(b) by 0 days.

(21) Appl. No.: 18/585,026

(22) Filed: Feb. 22, 2024

(65) Prior Publication Data
US 2024/0189127 A1   Jun. 13, 2024

Related U.S. Application Data (63) Continuation of application No. 17/202,155, filed on Mar. 15, 2021, now Pat. No. 12,011,379, which is a
(Continued)

(51) Int. Cl.
A61F 2/954     (2013.01)
A61B 17/00    (2006.01)
(Continued)

(52) U.S. Cl.
CPC ........ *A61F 2/954* (2013.01); *A61B 17/32056* (2013.01); *A61F 2/966* (2013.01); *A61M 25/0102* (2013.01); *A61M 25/0108* (2013.01); *A61M 25/1002* (2013.01); *A61B 2017/00358* (2013.01); *A61B 2017/2212* (2013.01);
(Continued)

(58) Field of Classification Search
CPC .... A61B 17/32056; A61B 2017/00358; A61B 2017/2212; A61F 2/954; A61F 2/966; A61M 25/01; A61M 25/0102; A61M 25/0108; A61M 25/1002;
(Continued)

(56) References Cited

U.S. PATENT DOCUMENTS

| | | |
|---|---|---|
| 3,896,815 A | 7/1975 | Fettel |
| 4,243,040 A | 1/1981 | Beecher |

(Continued)

FOREIGN PATENT DOCUMENTS

| | | |
|---|---|---|
| CN | 108472124 | 8/2018 |
| CN | 108472472 | 8/2018 |

(Continued)

OTHER PUBLICATIONS

International Search Report and Written Opinion for PCT/US2013/071271 dated Feb. 10, 2014, 7 pages.
EP 18725097.2 Extended Search Report dated Apr. 24, 2019, 9 pages.
(Continued)

*Primary Examiner* — Jocelin C Tanner
(74) *Attorney, Agent, or Firm* — Jennifer Hayes; Nixon Peabody LLP (57) ABSTRACT A guide sheath device with an integrated stabilization wire is provided. The guide sheath device includes an elongate member having a proximal and distal end and a lumen there between and a stabilization wire integrated to the elongate member.

21 Claims, 9 Drawing Sheets

Related U.S. Application Data continuation of application No. 16/183,150, filed on Nov. 7, 2018, now Pat. No. 11,007,075.

(60) Provisional application No. 62/631,904, filed on Feb. 18, 2018.

(51) Int. Cl.
*A61B 17/221* (2006.01)
*A61B 17/3205* (2006.01)
*A61F 2/966* (2013.01)
*A61M 25/01* (2006.01)
*A61M 25/06* (2006.01)
*A61M 25/10* (2013.01)

(52) U.S. Cl.
CPC ............. *A61M 2025/0177* (2013.01); *A61M 2025/0681* (2013.01)

(58) Field of Classification Search
CPC .. A61M 2025/0096; A61M 2025/0177; A61M 2025/0681
See application file for complete search history.

(56) References Cited

U.S. PATENT DOCUMENTS

| | | |
|---|---|---|
| 4,790,331 A | 12/1988 | Okada et al. |
| 5,098,707 A | 3/1992 | Baldwin et al. |
| 5,293,772 A | 3/1994 | Carr, Jr. |
| 5,344,426 A | 9/1994 | Lau et al. |
| 5,419,777 A | 5/1995 | Hofling |
| 5,433,705 A | 7/1995 | Giebel et al. |
| 5,571,135 A | 11/1996 | Fraser et al. |
| 5,651,366 A | 7/1997 | Liang et al. |
| 5,662,703 A | 9/1997 | Yurek et al. |
| 5,669,924 A | 9/1997 | Shaknovich |
| 5,690,644 A | 11/1997 | Yurek et al. |
| 5,718,702 A | 2/1998 | Edwards |
| 5,720,735 A | 2/1998 | Dorros |
| 5,766,192 A | 6/1998 | Zacca |
| 5,807,330 A | 9/1998 | Teitelbaum |
| 5,813,976 A | 9/1998 | Filipi et al. |
| 5,824,055 A | 10/1998 | Spiridigliozzi |
| 5,957,901 A | 9/1999 | Mottola et al. |
| 5,997,563 A | 12/1999 | Kretzers |
| 6,027,462 A | 2/2000 | Greene et al. |
| 6,059,813 A | 5/2000 | Vrba et al. |
| 6,070,589 A | 6/2000 | Keith et al. |
| 6,152,141 A | 11/2000 | Stevens et al. |
| 6,238,410 B1 | 5/2001 | Vrba et al. |
| 6,245,017 B1 | 6/2001 | Hashimoto |
| 6,245,573 B1 | 6/2001 | Spillert |
| 6,428,567 B2 | 8/2002 | Wilson et al. |
| 6,450,964 B1 | 9/2002 | Webler |
| 6,464,665 B1 | 10/2002 | Heuser |
| 6,494,875 B1 | 12/2002 | Mauch |
| 6,544,278 B1 | 4/2003 | Vrba et al. |
| 6,652,556 B1 | 11/2003 | Vantassel |
| 6,663,613 B1 | 12/2003 | Lewis et al. |
| 6,764,505 B1 | 7/2004 | Hossainy et al. |
| 6,780,174 B2 | 8/2004 | Mauch |
| 6,808,520 B1 | 10/2004 | Fouirkas et al. |
| 6,837,881 B1 | 1/2005 | Barbut |
| 6,929,633 B2 | 8/2005 | Evans et al. |
| 6,932,829 B2 | 8/2005 | Majercak |
| 6,942,682 B2 | 9/2005 | Vrba et al. |
| 7,235,083 B1 | 6/2007 | Perez et al. |
| 7,393,358 B2 | 7/2008 | Malewicz |
| 7,651,520 B2 | 1/2010 | Fischell et al. |
| 7,674,493 B2 | 3/2010 | Hossainy et al. |
| 7,740,791 B2 | 6/2010 | Kleine et al. |
| 7,758,624 B2 | 7/2010 | Dorn et al. |
| 7,763,010 B2 | 7/2010 | Evans et al. |
| 7,766,961 B2 | 8/2010 | Patel et al. |
| 7,828,832 B2 | 11/2010 | Belluche et al. |
| 7,842,026 B2 | 11/2010 | Cahill et al. |
| 7,955,370 B2 | 6/2011 | Gunderson |
| 8,092,509 B2 | 1/2012 | Dorn et al. |
| 8,119,184 B2 | 2/2012 | Hossainy et al. |
| 8,202,309 B2 | 6/2012 | Styrc |
| 8,241,241 B2 | 8/2012 | Evans et al. |
| 8,343,181 B2 | 1/2013 | Duffy et al. |
| 8,419,767 B2 | 4/2013 | Al-Qbandi et al. |
| 8,535,290 B2 | 9/2013 | Evans et al. |
| 8,721,714 B2 | 5/2014 | Kelley |
| 8,727,988 B2 | 5/2014 | Flaherty et al. |
| 8,728,144 B2 | 5/2014 | Fearnot |
| 8,740,971 B2 | 6/2014 | Iannelli |
| 8,986,241 B2 | 3/2015 | Evans et al. |
| 8,998,894 B2 | 4/2015 | Mauch et al. |
| 9,301,830 B2 | 4/2016 | Heuser et al. |
| 9,314,499 B2 | 4/2016 | Wang et al. |
| 9,414,824 B2 | 8/2016 | Fortson |
| 9,636,244 B2 | 5/2017 | Syed |
| 9,855,705 B2 | 1/2018 | Wang et al. |
| 9,980,838 B2 | 5/2018 | Syed |
| 10,492,936 B2 | 12/2019 | Syed |
| 10,779,976 B2 | 9/2020 | Syed |
| 10,857,014 B2 | 12/2020 | Syed |
| 10,888,445 B2 | 1/2021 | Syed |
| 11,007,075 B2 | 5/2021 | Bagoaisan |
| 11,020,256 B2 | 6/2021 | Syed |
| 2001/0003985 A1 | 6/2001 | Lafontaine et al. |
| 2001/0049534 A1 | 12/2001 | Lachat |
| 2002/0077691 A1 | 6/2002 | Nachtigall |
| 2002/0123698 A1 | 9/2002 | Garibotto et al. |
| 2002/0156518 A1 | 10/2002 | Tehrani |
| 2002/0165535 A1 | 11/2002 | Lesh |
| 2003/0088187 A1 | 5/2003 | Saadat et al. |
| 2003/0204171 A1 | 10/2003 | Kucharczyk |
| 2003/0216721 A1 | 11/2003 | Diederich |
| 2003/0229282 A1 | 12/2003 | Burdette |
| 2004/0002714 A1 | 1/2004 | Weiss |
| 2004/0073190 A1 | 4/2004 | Deem et al. |
| 2004/0138734 A1 | 7/2004 | Chobotov et al. |
| 2004/0147837 A1 | 7/2004 | Macaulay et al. |
| 2005/0043779 A1 | 2/2005 | Wilson |
| 2005/0101968 A1 | 5/2005 | Dadourian |
| 2005/0113798 A1 | 5/2005 | Slater |
| 2005/0113862 A1 | 5/2005 | Besselink et al. |
| 2005/0222488 A1 | 10/2005 | Chang et al. |
| 2005/0234499 A1 | 10/2005 | Olson et al. |
| 2005/0251160 A1 | 11/2005 | Saadat et al. |
| 2005/0267010 A1 | 12/2005 | Goodson et al. |
| 2006/0025752 A1 | 2/2006 | Broaddus et al. |
| 2006/0025844 A1 | 2/2006 | Majercak et al. |
| 2006/0030923 A1 | 2/2006 | Gunderson |
| 2006/0074484 A1 | 4/2006 | Huber |
| 2006/0155363 A1 | 7/2006 | Laduca et al. |
| 2006/0200221 A1 | 9/2006 | Malewicz |
| 2006/0257389 A1 | 11/2006 | Binford |
| 2006/0259063 A1 | 11/2006 | Bates et al. |
| 2006/0270900 A1 | 11/2006 | Chin et al. |
| 2007/0016019 A1 | 1/2007 | Salgo |
| 2007/0016062 A1 | 1/2007 | Park |
| 2007/0038061 A1 | 2/2007 | Huennekens et al. |
| 2007/0038293 A1 | 2/2007 | St.Goar et al. |
| 2007/0049867 A1 | 3/2007 | Shindelman |
| 2007/0083215 A1 | 4/2007 | Hamer et al. |
| 2007/0118151 A1 | 5/2007 | Davidson |
| 2007/0129719 A1 | 6/2007 | Kendale et al. |
| 2007/0219614 A1* | 9/2007 | Hartley ............. A61F 2/07 623/1.11 |
| 2007/0288082 A1 | 12/2007 | Williams |
| 2008/0009829 A1 | 1/2008 | Ta |
| 2008/0039746 A1 | 2/2008 | Hissong et al. |
| 2008/0114239 A1 | 5/2008 | Randall et al. |
| 2008/0194993 A1 | 8/2008 | Mclaren et al. |
| 2008/0208309 A1* | 8/2008 | Saeed ............. A61F 2/954 623/1.11 |
| 2008/0281398 A1 | 11/2008 | Koss |
| 2008/0306467 A1 | 12/2008 | Reydel |
| 2009/0005679 A1 | 1/2009 | Dala-Krishna |

(56) References Cited

U.S. PATENT DOCUMENTS

| | | |
|---|---|---|
| 2009/0018526 A1 | 1/2009 | Power et al. |
| 2009/0036780 A1 | 2/2009 | Abraham |
| 2009/0132019 A1 | 5/2009 | Duffy et al. |
| 2009/0171293 A1 | 7/2009 | Yang et al. |
| 2009/0177035 A1 | 7/2009 | Chin |
| 2009/0240253 A1 | 9/2009 | Murray |
| 2009/0254116 A1 | 10/2009 | Rosenschein et al. |
| 2009/0270975 A1 | 10/2009 | Giofford, III et al. |
| 2009/0319017 A1 | 12/2009 | Berez et al. |
| 2010/0016943 A1 | 1/2010 | Chobotov |
| 2010/0024818 A1 | 2/2010 | Stenzler et al. |
| 2010/0030165 A1 | 2/2010 | Takagi et al. |
| 2010/0030256 A1 | 2/2010 | Dubrul et al. |
| 2010/0069852 A1 | 3/2010 | Kelley |
| 2010/0168583 A1 | 7/2010 | Dausch et al. |
| 2010/0185161 A1 | 7/2010 | Pellegrino et al. |
| 2010/0185231 A1 | 7/2010 | Lashinski |
| 2010/0204708 A1 | 8/2010 | Sharma |
| 2010/0211095 A1 | 8/2010 | Carpenter |
| 2010/0268067 A1 | 10/2010 | Razzaque et al. |
| 2010/0272740 A1 | 10/2010 | Vertegel et al. |
| 2010/0298922 A1 | 11/2010 | Thornton et al. |
| 2011/0009943 A1 | 1/2011 | Paul et al. |
| 2011/0034987 A1 | 2/2011 | Kennedy |
| 2011/0071394 A1 | 3/2011 | Fedinec |
| 2011/0082533 A1 | 4/2011 | Vardi et al. |
| 2011/0098681 A1 | 4/2011 | Djurivic |
| 2011/0196420 A1 | 8/2011 | Ebner |
| 2011/0224773 A1 | 9/2011 | Gifford et al. |
| 2011/0230830 A1 | 9/2011 | Gifford, III et al. |
| 2011/0270375 A1 | 11/2011 | Hartley et al. |
| 2012/0016343 A1 | 1/2012 | Gill |
| 2012/0020942 A1 | 1/2012 | Hall et al. |
| 2012/0022636 A1 | 1/2012 | Chobotov |
| 2012/0029478 A1 | 2/2012 | Kurosawa |
| 2012/0034205 A1 | 2/2012 | Alkon |
| 2012/0035590 A1 | 2/2012 | Whiting et al. |
| 2012/0046690 A1 | 2/2012 | Blom |
| 2012/0169712 A1 | 7/2012 | Hill et al. |
| 2012/0209375 A1 | 8/2012 | Madrid et al. |
| 2012/0221094 A1 | 8/2012 | Cunningham |
| 2012/0289945 A1 | 11/2012 | Segermark |
| 2013/0053792 A1 | 2/2013 | Fischell et al. |
| 2013/0131777 A1 | 5/2013 | Hartley et al. |
| 2013/0218201 A1 | 8/2013 | Obermiller |
| 2013/0296773 A1 | 11/2013 | Feng et al. |
| 2013/0310823 A1 | 11/2013 | Gelfand et al. |
| 2013/0331819 A1 | 12/2013 | Rosenman et al. |
| 2013/0331921 A1 | 12/2013 | Roubin |
| 2014/0031925 A1 | 1/2014 | Garrison et al. |
| 2014/0114346 A1 | 4/2014 | Mccaffrey |
| 2014/0142427 A1 | 5/2014 | Petroff |
| 2014/0214002 A1 | 7/2014 | Thermopeutix |
| 2014/0228808 A1 | 8/2014 | Webster et al. |
| 2014/0276602 A1 | 9/2014 | Bonnette |
| 2014/0358123 A1 | 12/2014 | Ueda et al. |
| 2015/0018942 A1 | 1/2015 | Hung et al. |
| 2015/0174377 A1 | 6/2015 | Syed |
| 2015/0190576 A1 | 7/2015 | Lee et al. |
| 2015/0201900 A1 | 7/2015 | Syed |
| 2015/0245933 A1 | 9/2015 | Syed |
| 2015/0352331 A1 | 12/2015 | Helm, Jr. |
| 2015/0366536 A1 | 12/2015 | Courtney et al. |
| 2015/0374261 A1 | 12/2015 | Grunwald |
| 2016/0008058 A1 | 1/2016 | Hu et al. |
| 2016/0038724 A1 | 2/2016 | Madsen et al. |
| 2016/0120509 A1 | 5/2016 | Syed |
| 2016/0120673 A1 | 5/2016 | Siegel et al. |
| 2016/0296355 A1 | 10/2016 | Syed |
| 2016/0338835 A1 | 11/2016 | Van Bladel et al. |
| 2017/0119562 A1 | 5/2017 | Syed |
| 2017/0119563 A1 | 5/2017 | Syed |
| 2017/0135833 A1 | 5/2017 | Syed |
| 2017/0181876 A1 | 6/2017 | Syed |
| 2017/0304095 A1 | 10/2017 | Syed |
| 2017/0361062 A1 | 12/2017 | Syed |
| 2018/0042743 A1 | 2/2018 | Syed |
| 2018/0059124 A1 | 3/2018 | Syed |
| 2018/0116780 A1 | 5/2018 | Laine |
| 2018/0250147 A1 | 9/2018 | Syed |
| 2019/0091441 A1 | 3/2019 | Syed |
| 2019/0336114 A1 | 11/2019 | Syed |
| 2020/0038210 A1 | 2/2020 | Syed |
| 2021/0196492 A1 | 7/2021 | Bagaoisan |
| 2022/0152347 A1 | 5/2022 | Syed |

FOREIGN PATENT DOCUMENTS

| | | |
|---|---|---|
| CN | 108882975 | 11/2018 |
| CN | 109475722 | 3/2019 |
| CN | 111629696 | 9/2020 |
| EP | 3280355 | 2/2018 |
| EP | 3367969 | 9/2018 |
| EP | 3368123 | 9/2018 |
| EP | 3399944 | 11/2018 |
| EP | 3405261 | 11/2018 |
| EP | 3471815 | 4/2019 |
| IN | 201827018555 | 10/2018 |
| IN | 201827018768 | 10/2018 |
| WO | WO 1996/036269 | 11/1996 |
| WO | WO 1999/40849 | 8/1999 |
| WO | WO 2004/089249 | 10/2004 |
| WO | WO 2010/129193 | 11/2010 |
| WO | WO 2011/011539 | 1/2011 |
| WO | WO 2011/106502 | 9/2011 |
| WO | WO 2011/137336 | 11/2011 |
| WO | WO 2012/030101 | 8/2012 |
| WO | WO 2014/081947 | 5/2014 |
| WO | WO 2014/197839 | 12/2014 |
| WO | WO 2016164215 | 10/2016 |
| WO | WO 2017/074492 | 5/2017 |
| WO | WO 2017/074536 | 5/2017 |
| WO | WO 2017/127127 | 7/2017 |
| WO | WO 2017/222571 | 12/2017 |
| WO | WO 2017/222612 | 12/2017 |
| WO | WO 2018/164766 | 9/2018 |
| WO | WO 2019/070349 | 4/2019 |

OTHER PUBLICATIONS

International Search Report and Written Opinion for PCT/US2016/024794 dated Jul. 1, 2016, 10 pages.
International Search Report and Written Opinion for PCT/US2016/024795 dated Aug. 30, 2016, 14 pages.
International Search Report and Written Opinion for PCT/US2016/047163 dated Oct. 28, 2016, 9 pages.
International Search Report and Written Opinion for PCT/US2016/047165 dated Jan. 5, 2017, 13 pages.
International Search Report and Written Opinion for PCT/US2017/021188 dated May 10, 2017, 11 pages.
International Search Report and Written Opinion for PCT/US2018/012834 dated Mar. 15, 2018, 13 pages.
International Search Report and Written Opinion for PCT/US2018/047372 dated Jan. 2, 2019, 8 pages.
International Search Report and Written Opinion for PCT/US2019/012727 dated Mar. 21, 2019, 12 pages.
International Search Report and Written Opinion for PCT/US2019/12745 dated Apr. 1, 2019, 10 pages.
International Preliminary Report on Patentability for PCT/US2013/071271 dated May 26, 2015, 6 pages.
International Preliminary Report on Patentability for PCT/US2016/024795 dated May 1, 2018, 10 pages.
International Preliminary Report on Patentability for PCT/US2016/047165 dated May 1, 2018, 5 pages.
International Preliminary Report on Patentability for PCT/US2017/021188 dated Dec. 25, 2018, 9 pages.
International Preliminary Report on Patentability for PCT/US2016/047163 dated Dec. 25, 2018, 7 pages.
EP 16777055.1 Extended Search Report dated Feb. 12, 2019, 7 pages.

(56) References Cited

OTHER PUBLICATIONS

EP 16860437.9 Extended Search Report dated May 17, 2019.
EP 16906475.5 Extended Search Report dated Jan. 24, 2020.
EP 17815838.2 Extended Search Report dated Jan. 20, 2020.
Beckman et al., Venous Thromboembolism: A Public Health Concern, Am J Prev Med., 2010, vol. 38(4), pp. S495-S501.
Blaney et al., Alteplase for the Treatment of Central Venous Catheter Occlusion in Children: Results of a Prospective, Open-Label, Single-Arm Study (The Cathflo Activase Pediatric Study), J Vasc Interv Radiol, 2006, vol. 17(11), pp. 1745-1751.
Godwin, J., The Circulatory and Respiratory Systems, Z0250 Lab III, 2002, retrieved from: https://projects.ncsu.edu/cals/course/zo250/lab-3.html.
Meunier et al., Individual Lytic Efficacy of Recombinant Tissue Plasminogen Activator in an in-vitro Human Clot Model: Rate of Nonresponse Acad Emerg Med., 2013, vol. 20(5), pp. 449-455.
Schwartz et al., Intracardiac Echocardiography in Humans using a Small-Sized (6F), Low Frequency (12.5 MHz) Ultrasound Catheter Methods, Imaging Planes and Clinical Experience, Journal of the American College of Cardiology, 1993, vol. 21(1), pp. 189-198.
Shah, T., Radiopaque Polymer Formulations for Medical Devices, MDDI Medical Diagnostic and Device Industry: Materials, 2001, retrieved from: https://www.mddionline.com/radiopaque-polymer-formulations-medical-devices.
Tripathi et al., Use of Tissue Plasminogen Activator for Rapoid Dissolution of Fibrin and Blood Clots in the Eye After Surgery for Claucomoa and Cataract in Humans, Drug Development Research, 1992, vol. 27(2), pp. 147-159.
Stroke Treatments, American Heart Association, Retrieved from: http://www.strokeassociation.org/STROKEORG/AboutStroke/Treatment/Stroke-Treatments_UCM_310892_Article.jsp#V9Hrg2WfV_1 on Sep. 8, 2016.

* cited by examiner

VASCULAR ACCESS DEVICES AND METHODS FOR LOWER LIMB INTERVENTIONS

CROSS REFERENCE TO RELATED APPLICATIONS

This application is a continuation application of U.S. patent application Ser. No. 17/202,155, filed Mar. 15, 2021, entitled, entitled "VASCULAR ACCESS DEVICES AND METHODS FOR LOWER LIMB INTERVENTIONS", which is a continuation of U.S. patent application Ser. No. 16/183,150, filed Nov. 7, 2018, entitled "VASCULAR ACCESS DEVICES AND METHODS FOR LOWER LIMB INTERVENTIONS", which claims priority under 35 U.S.C. § 119 to U.S. Provisional Application No. 62/631,904, entitled "MODIFIED FIXED FLAT WIRE BIFURCATED CATHETER AND ITS APPLICATION IN AORTO BIFEMORAL BYPASS," and filed on Feb. 18, 2018. The contents of those applications are hereby incorporated by reference in their entirety.

TECHNICAL FIELD

The present disclosure relates to improved methods and apparatuses implemented in endovascular procedures involving tortuous vasculature. Specifically, the present disclosure relates to vascular access devices and methods for accessing angulated and tortuous aortic bifurcations, tortuous lower extremity vessels and supporting the pushability of endovascular tools.

BACKGROUND

Stenting and balloon angioplasty of arteries are considered to be well characterized interventional procedures. Typically, stent placement and balloon angioplasty are performed to re-establish or normalize blood flow within the artery that may have been constricted by plaque or embolic deposits. In such procedures, vascular access in the lower extremities is often performed via a retrograde, antegrade or transpedal approach.

Antegrade access is an industry standard as it provides superior support when advancing interventional devices through relatively-straight blood vessels. However, the antegrade access procedure can be technically demanding and typically presents significant challenges in obese patients where the femoral artery may be difficult to locate in the patient's soft tissue. Furthermore, antegrade punctures that occur during the antegrade access procedure can also elicit complications (e.g. hematoma, pseudo aneurysm, hemorrhage) related to closure of the puncture site at the femoral artery access point.

The retrograde contralateral approach is the most common technique for accessing the lower limbs where an access point at the femoral artery located on one side of the body (i.e. the contralateral side) is used to access the blood vessels and lesions in the other leg on the ipsilateral side. This retrograde access is technically simple in most patients and feasible for all interventionalists. However, the retrograde procedure may present challenges when accessing the vasculature and anatomies targeted for treatment based on the anatomical disposition of the access location. For example, vascular access in a hostile anatomy with tortuous peripheral vessels and intervention of distal most blood vessels (e.g. in the popliteal and tibial arteries) can be challenging or impossible, for example, in highly tortuous vessels containing calcific plaques and/or in highly angulated aortic bifurcations.

The transpedal access procedure is a relatively new approach wherein support catheters and guidewires leverage the enhanced support provided by access of blood vessels from the foot. The pedal artery typically used for access is small and existing interventional tools are not optimally sized. This is a significant drawback because irreversible damage to tenuous blood vessels in the foot can further exacerbate the condition of patients with critical limb ischemia.

Although endovascular devices (e.g. stent delivery systems, angioplasty balloons, atherectomy devices, thrombectomy devices, etc.) are generally designed to accommodate very acute bends and tortuous anatomies in the lower extremities, these devices rely on the use of rigid guide catheters, guide sheaths and guide wires to be delivered to the target treatment site(s). When long delivery systems or other catheters are used, the performance characteristics (i.e. pushability) of these catheters and the support provided by the guide catheters, guide sheaths and guide wires become critical. As a result, guide catheters, guide sheaths and guide wires of adequate rigidity and structure are needed to most effectively manipulate these interventional devices in tortuous anatomies. Often times, tortuous arteries and access vessels can be injured during the insertion, manipulation and stabilization of the interventional tools being used during the procedure using the rigid guide catheters, guide sheaths and guide wires. Injuries can be caused by perforation or dissection of the arterial wall by the stiff guide catheters, guide sheaths and guide wires, often resulting in hemorrhage, thrombus formation leading to infarcts or even death.

Thus, there exists a need for improved methods and apparatuses that can be easily positioned and subsequently provide superior support and stability to the interventional devices to be used in a procedure thereby reducing injuries and trauma caused to the arterial walls during vascular access, and allowing faster navigation and access through difficult anatomy.

SUMMARY

A guide sheath apparatus configured to perform endovascular procedures is disclosed herein. The apparatus includes an elongate member with a proximal and distal end and a lumen there between. In some embodiments, the lumen is capable of allowing passage of guide wires. The apparatus also includes a stabilization wire integrated within the elongate member. In some embodiments, the stabilization wire extends beyond the distal tip of the elongate member. The stabilization wire can include either a round or flat material. The stabilization wire can bifurcate away from the surface of the elongate member.

The apparatus can also include a removable dilator having an elongate member with proximal and distal end and a lumen there-between. In some embodiments, the apparatus can include a tool configured to anchor the stabilization wire in place.

The elongate member can include at least one radiopaque marker. In some embodiments, a transition point of bifurcation is located between the proximal and distal end of the elongate member. The transition point of bifurcation can include a radiopaque marker. In some embodiments, the elongate member includes a radiopaque filler.

A method for performing an endovascular procedure is also provided. The method includes obtaining bilateral, percutaneous retrograde access sites in the left and right common femoral arteries. The method also includes inserting a guide sheath with an integrated stabilization wire. The guide sheath includes a radiopaque tip at its distal end configured to be advanced through the contralateral access site.

The method also includes inserting a snare device into an ipsilateral access site. The snare device includes a snare catheter which contains a coaxial snare wire that has a snare loop at the distal end. The method further includes capturing the stabilization wire with the snare device. In some embodiments, capturing the stabilization wire can include positioning and cinching a distal end of the stabilization wire inside the snare loop under fluoroscopic visualization. The method also includes externalizing the stabilization wire at the ipsilateral access site. In some embodiments, externalizing the stabilization wire includes applying a tensile force to the snare device and a push force to the guide sheath. In some embodiments, the stabilization wire is externalized to position the elongate member at or about the ipsilateral access site. The method also includes reversibly anchoring the externalized stabilization wire at the ipsilateral access site.

Additional features and advantages of the disclosure will be set forth in the description that follows, and in part, will be obvious from the description; or can be learned by practice of the principles disclosed herein. The features and advantages of the disclosure can be realized and obtained by means of the instruments and combinations particularly pointed out in the appended claims. These and other features of the disclosure will become fully apparent from the following description and appended claims, or can be learned by the practice of the principles set forth herein.

BRIEF DESCRIPTION OF THE DRAWINGS

In order to describe the manner in which the above-recited disclosure and its advantages and features can be obtained, a more particular description of the principles described above will be rendered by reference to specific examples illustrated in the appended drawings. These drawings depict only example aspects of the disclosure, and are therefore not to be considered as limiting of its scope. These principles are described and explained with additional specificity and detail through the use of the following drawings.

The present disclosure is susceptible to various modifications and alternative forms. Some representative embodiments have been shown by way of example in the drawings and will be described in detail herein. It should be understood, however, that the invention is not intended to be limited to the particular forms disclosed. Rather, the disclosure is to cover all modifications, equivalents, and alternatives falling within the spirit and scope of the invention as defined by the appended claims.

DETAILED DESCRIPTION OF ILLUSTRATED EMBODIMENTS

The present invention is described with reference to the attached figures, where like reference numerals are used throughout the figures to designate similar or equivalent elements. The figures are not drawn to scale, and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details, or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present disclosure.

Figure 1:
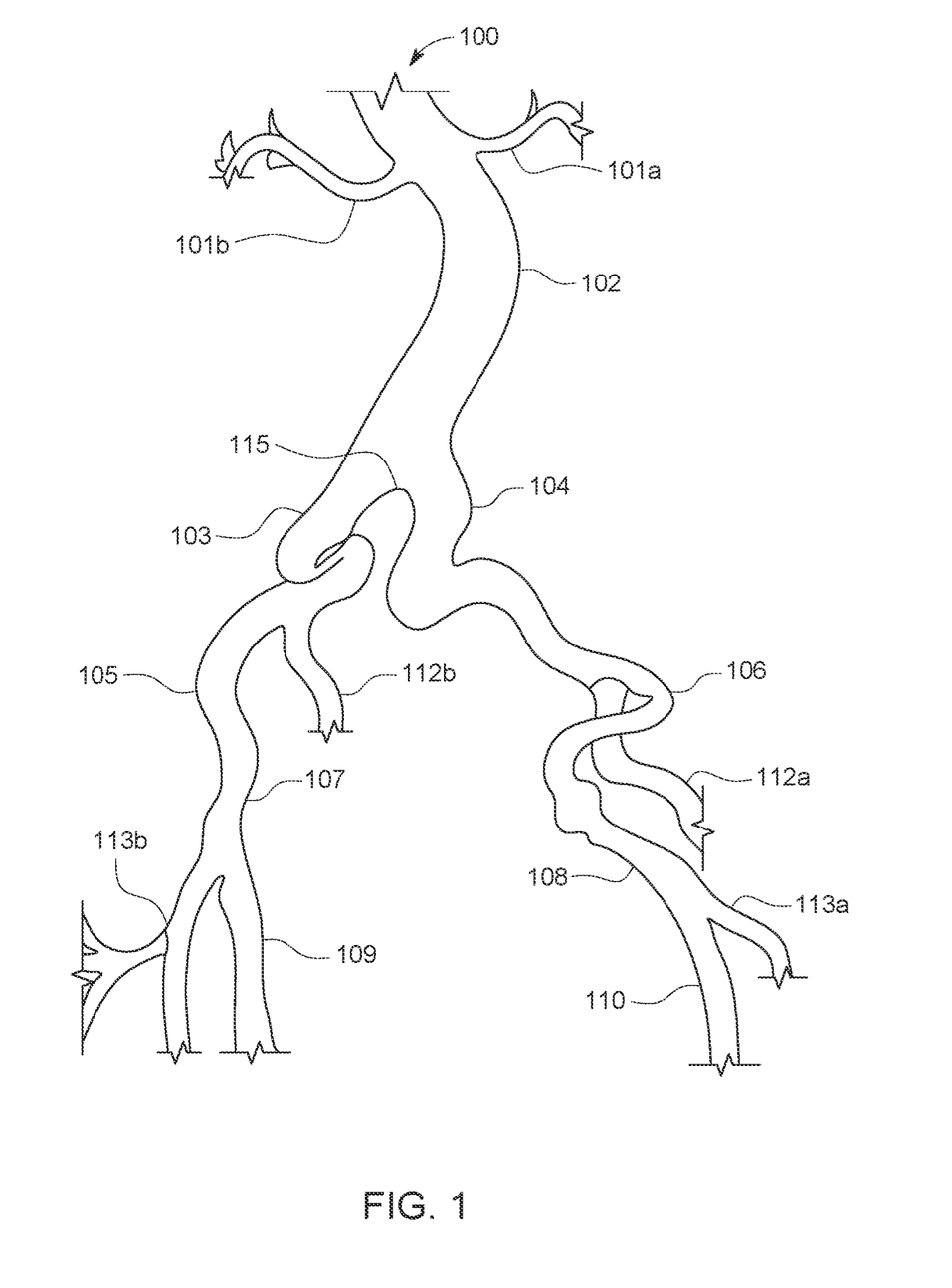
FIG. 1 illustrates an aortic bifurcation and tortuous vessel anatomy, in accordance with an embodiment of this disclosure.

FIG. 1 illustrates an aortic bifurcation and tortuous peripheral artery 100, in accordance with an embodiment of this disclosure. The tortuous peripheral artery 100 can include an abdominal aortic bifurcation with tortuous branch arteries. The tortuous branch arteries can include a right renal artery 101b and a left renal artery 101a extending from an abdominal aorta 102. The abdominal aorta 102 can be parted at an aortic bifurcation 115, and connected to arteries of the lower limbs. The arteries of the lower limbs can include a right common iliac 103 and a left common iliac 104. The left common iliac 104 can be split into a left external iliac 106 and a left internal iliac 112a. The left external iliac 106 can be connected to a left common femoral 108, and further split into a left deep femoral 113a, and a left superficial femoral 110. The The right common iliac 103 can be connected to a right external iliac 105. The right external iliac 105 can be connected to a right common femoral 107, which splits into a right deep femoral 113b and a right superficial femoral 109. FIG. 1 illustrates the tortuous nature of the peripheral arteries.

When performing interventions within the tortuous peripheral artery 100, it is common to encounter difficulties associated with access and pushability. For example, a highly angulated aortic bifurcation 115 or the extremely tortuous common iliac arteries 103 and 104 can be extremely difficult to traverse. Furthermore, these arteries can contain calcific plaques or other obstructions which can add anatomic and technical challenges when traversing the tortuous peripheral artery 100.

Figure 2:
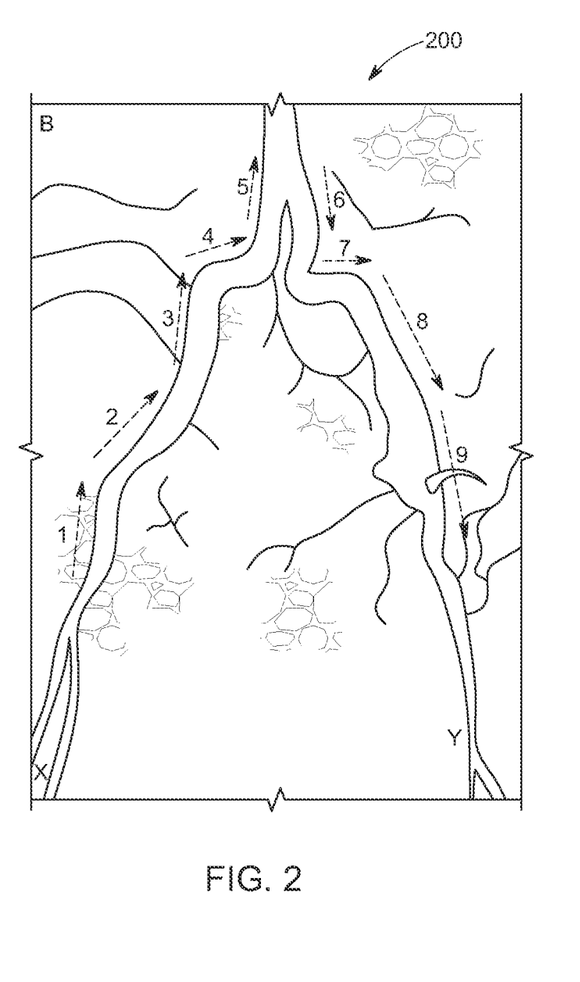
FIG. 2 illustrates a tortuous anatomical pathway from the percutaneous access within the common femoral artery on the contralateral side to a potential procedure location in the artery on the ipsilateral side, in accordance with an embodiment of the disclosure.

FIG. 2 illustrates a tortuous anatomical pathway 200 from the percutaneous access within the common femoral artery on the contralateral side to a potential procedure location on the ipsilateral side, in accordance with an embodiment of the disclosure. In some embodiments, interventional devices such as wires and catheters are pushed from the contralateral access at point 'X' to the treatment site 'Y'. The devices would need to travel through the general pathways 1 through 9. Due to the multi directional twists and turns along the pathways 1 through 9, the devices can suffer from a significant loss of performance such as torque and pushability. While FIG. 2 illustrates the tortuous anatomical pathway 200 in a two-dimensional format, the tortuousity of the anatomical pathway 200 is often significantly more severe, as illustrated in FIG. 1.

Figure 3A:
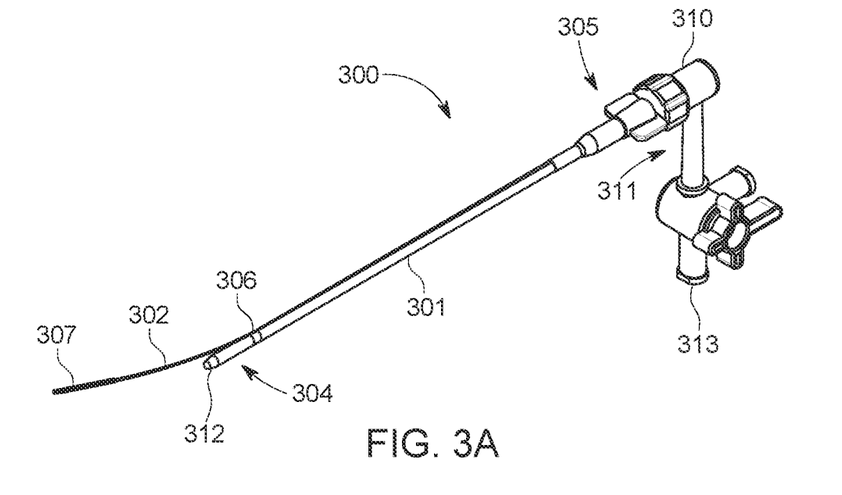
FIG. 3A illustrates a guide sheath with an integrated stabilization wire in accordance with an embodiment of the disclosure.

FIG. 3A illustrates a guide sheath 300 with an integrated stabilization wire 302 in accordance with an embodiment of the disclosure. The guide sheath 300 can include an elongate member 301 with a proximal end 305 and a distal end 304 located opposite of the proximal end 305. The elongate member 301 can be made up of materials commonly known in the art including, for example, metal tubing, reinforced or unreinforced polymeric tubing with or without radiopaque fillers, or combinations thereof. The metal tubing can include stainless steel, nickel titanium, cobalt chromium, copper, aluminum, or the like. The reinforced polymeric tubing can include braid or coil structures or combinations thereof. The reinforced polymeric tubing can be made up of stainless steel, nickel titanium, composites, metal reinforced polymer, polymer, or a combination thereof. The elongate member 301 can further include one or more radiopaque markers along its length, such as distal radiopaque marker 308 and proximal radiopaque marker 309. The radiopaque markers 308 and 309 can be at the distal tip or at the transition point of bifurcation and located between the proximal and distal end of the elongate member 301. Alternatively, the radiopaque markers 308 and 309 can be located between the midpoint and distal end of the elongate member 301.

The distal radiopaque marker 308 can provide visualization of the distal most tip of the elongate member 301 under fluoroscopy. The proximal radiopaque marker 309 can provide the user with a visual guidance as to the exact location of the stabilization wire transition 306 under fluoroscopy to aid in positioning at the ipsilateral access. The radiopaque markers 308 and 309 can be a coil, a tube fabricated using gold, platinum, iridium, barium sulfate loaded polymers, or a combination thereof. The radiopaque markers 308 and 309 can be attached to the elongate member 301 using welding, heat fusing, adhesive bonding, mechanical locking, crimping, laminating, soldering, or the like.

The proximal end 305 can include a hub with hemostasis valve 310 and a side port 311 that may include a stopcock with luer connector 313. The distal end 304 can include a stabilization wire transition 306 connected to the side wall of the elongate member 301. The hub with hemostasis valve 310 can be a valve and hemostatic device such as a touhy borst valve, duck-bill valve, o-ring, or a combination thereof. The hemostasis valve 310 can allow passage of procedural catheters and interventional devices through the lumen 312 of elongate member 301 while maintaining hemostasis. In some embodiments, the stopcock with luer connector 313 facilitates communication with the lumen 312 of the elongate member 301 and facilitates an injection of fluids, such as saline, contrast, $CO_2$ gas or medicines. The stabilization wire 302 bifurcates alongside the elongate member 301 at the stabilization wire transition 306 and extends beyond the distal section of the guide sheath 300. The stabilization wire 302 can include a distal segment 307.

In some embodiments, the stabilization wire 302 can be made up of a solid or hollow member with a cross-section that is round, flat, rectangular, or a combination thereof. The stabilization wire 302 can be fabricated using commonly known materials in the art including, for example, stainless steel, nickel titanium, composites, metal reinforced polymer, polymer, a combination thereof, or the like. The stabilization wire 302 can be attached to the elongate member 301 by methods known in the art including, for example, welding, heat fusing, adhesive bonding, mechanical locking, crimping, laminating, soldering, or the like.

The stabilization wire 302 can be connected to the elongate member 301 by a single point at the stabilization wire transition 306. In alternative embodiments, a proximal segment of the stabilization wire 302 can be embedded within or along at least some portion of an elongate member wall (not shown) within the elongate member 301. In addition, the distal segment 307 of the stabilization wire 302 can be reduced in size to enhance flexibility using methods commonly known in the art including, for example, centerless grinding, necking, drawing, cold working, and the like.

The distal segment 307 of the stabilization wire 302 can be made up of radiopaque material to provide enhanced visualization under fluoroscopic guidance. The radiopaque material can include a coil, a tube or the like. The radiopaque material can be fabricated using materials commonly known in the art including, for example, gold, platinum, iridium, barium sulfate loaded polymers, or a combinations thereof, or the like. The radiopaque material can be attached to the distal segment 307 of the stabilization wire 302 using methods commonly known in the art including, for example, welding, heat fusing, adhesive bonding, mechanical locking, crimping, laminating, soldering, or the like.

Figure 3B:
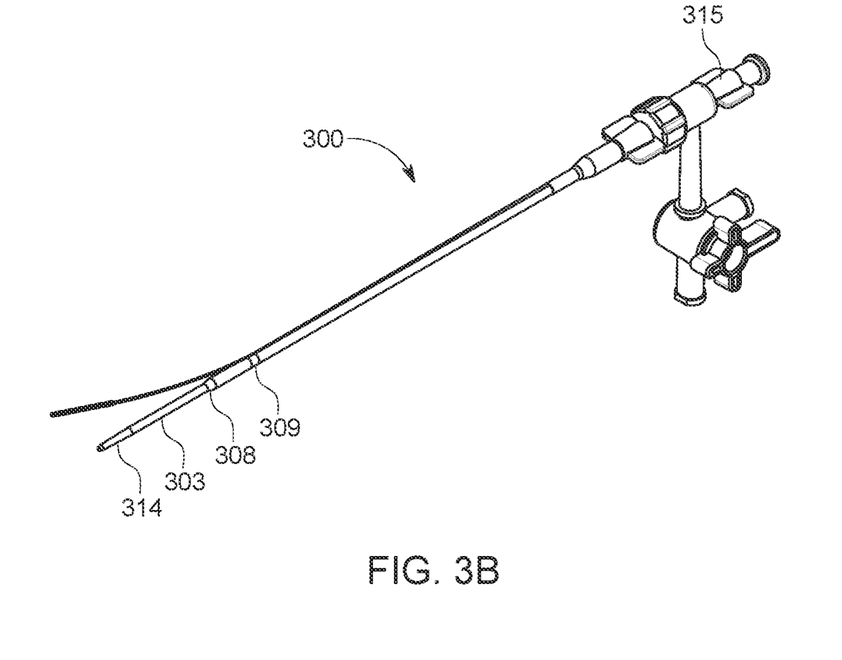
FIG. 3B illustrates a guide sheath of FIG. 3A with the addition of a dilator assembled within the lumen of the guide sheath in accordance with an embodiment of the disclosure.

FIG. 3B illustrates the guide sheath 300 with dilator 303 coaxially assembled within the guide sheath 300. The dilator 303 can include a distal end 314. In some embodiments, the dilator 303 can be assembled within the lumen 312 of the guide sheath 300. The dilator 303 can include a lumen (not shown) disposed along its length sized to facilitate passage of endovascular guide wires. The dilator 303 can be constructed using a rod or tube fabricated using methods and materials such as metallic and polymeric materials with or without radiopaque fillers (e.g. stainless steel, Nitinol, Pebax, high or low density Polyethylene, Nylon, Polypropylene, combinations thereof, or the like). The dilator 303 can be made using fabrication methods such as extrusion, drawing, injection molding, 3-D printing, or combinations thereof. The dilator distal end 314 can incorporate a tapered tip to smoothen the dimensional transition between the elongate member 301 to a guide wire (not shown) that may be disposed within the lumen (not shown) of the dilator 303. The proximal end of the dilator 303 can include a hub 315 that can be reversibly locked to the hub with hemostasis valve 310 of the guide sheath 300 to maintain the position of the dilator 303 relative to the guide sheath 300 during delivery to the target location.

FIGS. 4 to 8 illustrate an exemplary process for endovascular treatment of tortuous aortoiliac arteries implementing the guide sheath 300 with integrated stabilization wire 302, in accordance with an embodiment of the disclosure. Furthermore, FIGS. 4 to 8 illustrate the process of providing end-to-end stability to any procedural catheters and other interventional devices introduced through the procedural lumen 312 of the guide sheath 300.

Figure 4:
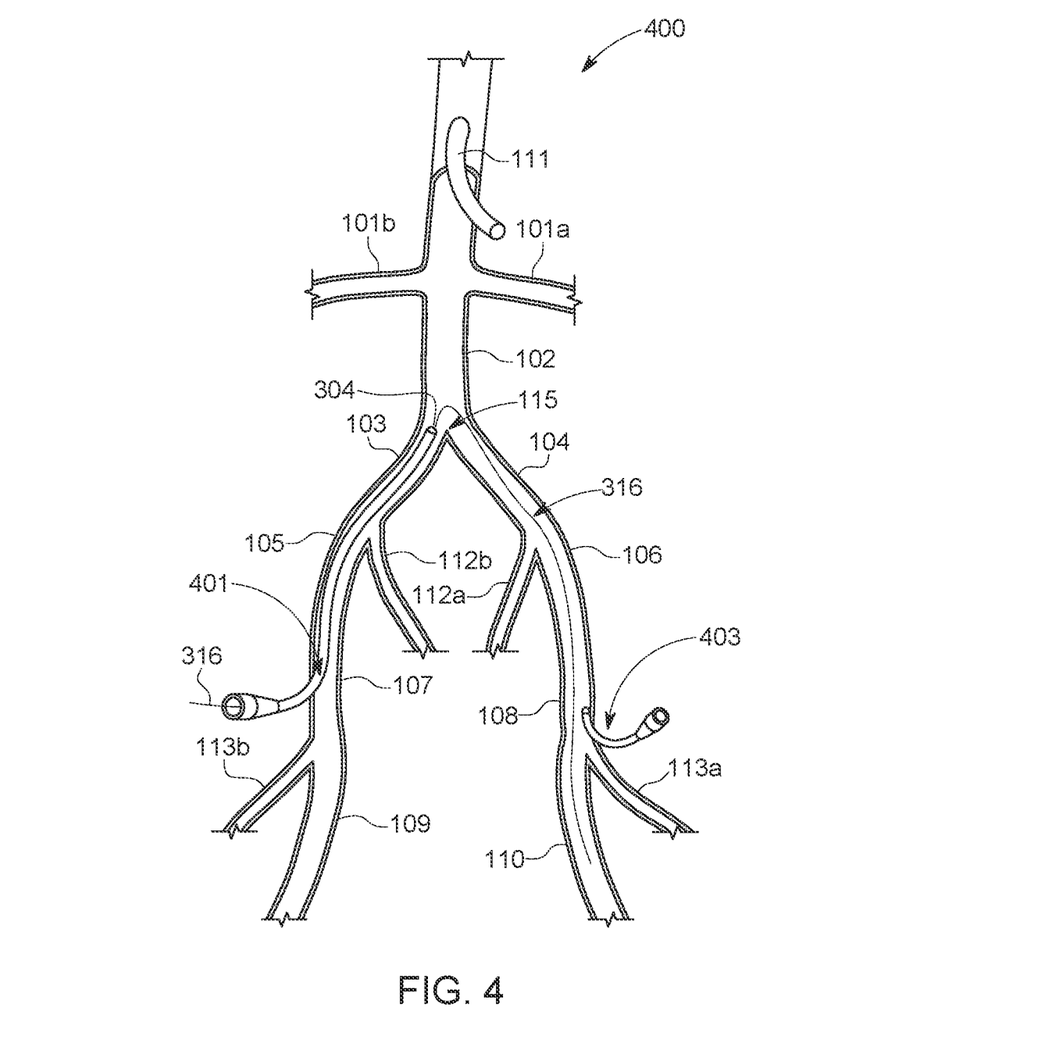
FIG. 4 illustrates a main access sheath placed through a percutaneous, contralateral femoral access, with its tip guided to the aortic bifurcation and a low profile, access sheath placed through a percutaneous, ipsilateral femoral access, in accordance with an embodiment of the disclosure.

FIG. 4 illustrates a diagram 400 where a main access sheath 401 is introduced percutaneously over an access guide wire 316 through the contralateral femoral access site 402 and into the right common femoral artery 107 using standard technique. The main access sheath 401 can include a 7 French vascular introducer sheath. The access guide wire 316 can typically be positioned such that it can gain access to the ipsilateral common femoral artery and/or to the ipsilateral vasculature. The dilator (not shown) of the main access sheath 401 can be loaded and advanced over the access guide wire 316 towards the right external iliac artery 105 and right common iliac artery 103 until the tip of main access sheath 401 reaches the aortic bifurcation 115.

Once the tip of main access sheath 401 reaches the aortic bifurcation 115, the main access sheath dilator (not shown) is removed while the main access sheath 401 and the access guide wire 316 are left in place. The main access sheath 401 can be positioned under fluoroscopic guidance with the aid of radiopaque tip marker 405. FIG. 4 also illustrates the percutaneous introduction of a low profile, ipsilateral femoral access sheath 403 through access site 404 to introduce a snare device (not shown) into the left common femoral artery 108 on the ipsilateral side. The ipsilateral femoral access sheath 403 can include a 4 French vascular introducer sheath.

Figure 5:
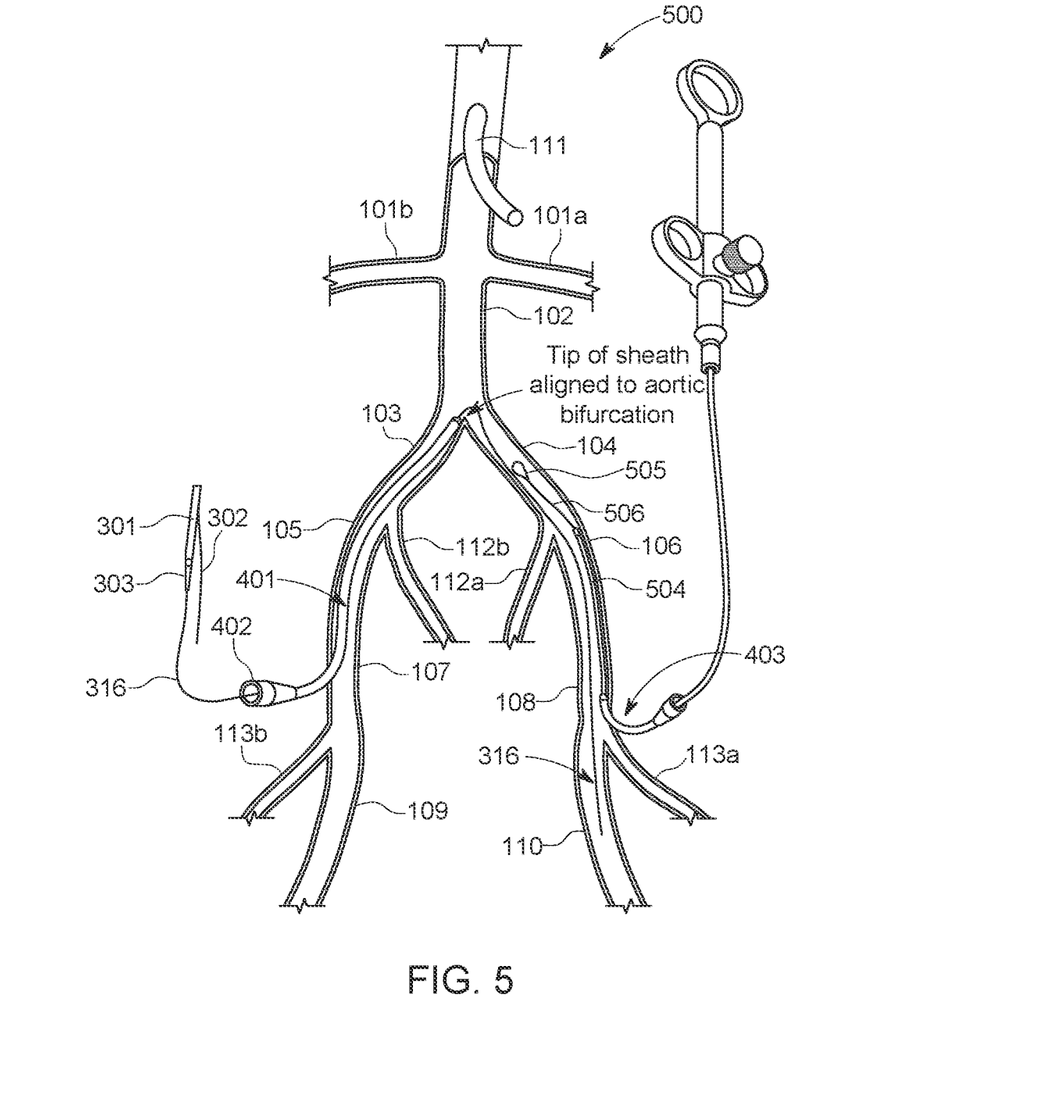
FIG. 5 illustrates a process of inserting a snare device into the main access sheath of FIG. 4 and advancing the snare device to the aortic bifurcation through the ipsilateral access, in accordance with an embodiment of the disclosure.

FIG. 5 illustrates a process of inserting a snare device 504 into the ipsilateral femoral access sheath 403 and advancing the snare catheter 504 to the aortic bifurcation through the ipsilateral access. The snare catheter 504 can include a snare wire 506 introduced through the ipsilateral femoral access sheath 403. The snare wire 506 can include a 20 to 30 mm (or smaller) snare loop 505 at its distal end. The snare catheter 504 can be advanced towards the aortic bifurcation 115 to position the snare loop 505 in the abdominal aorta to accept and capture the stabilization wire 302. The dilator 303 of guide sheath 300 can be loaded over the access guide wire 316 and positioned close to the proximal hub 402 of the main access sheath 401.

Figure 6:
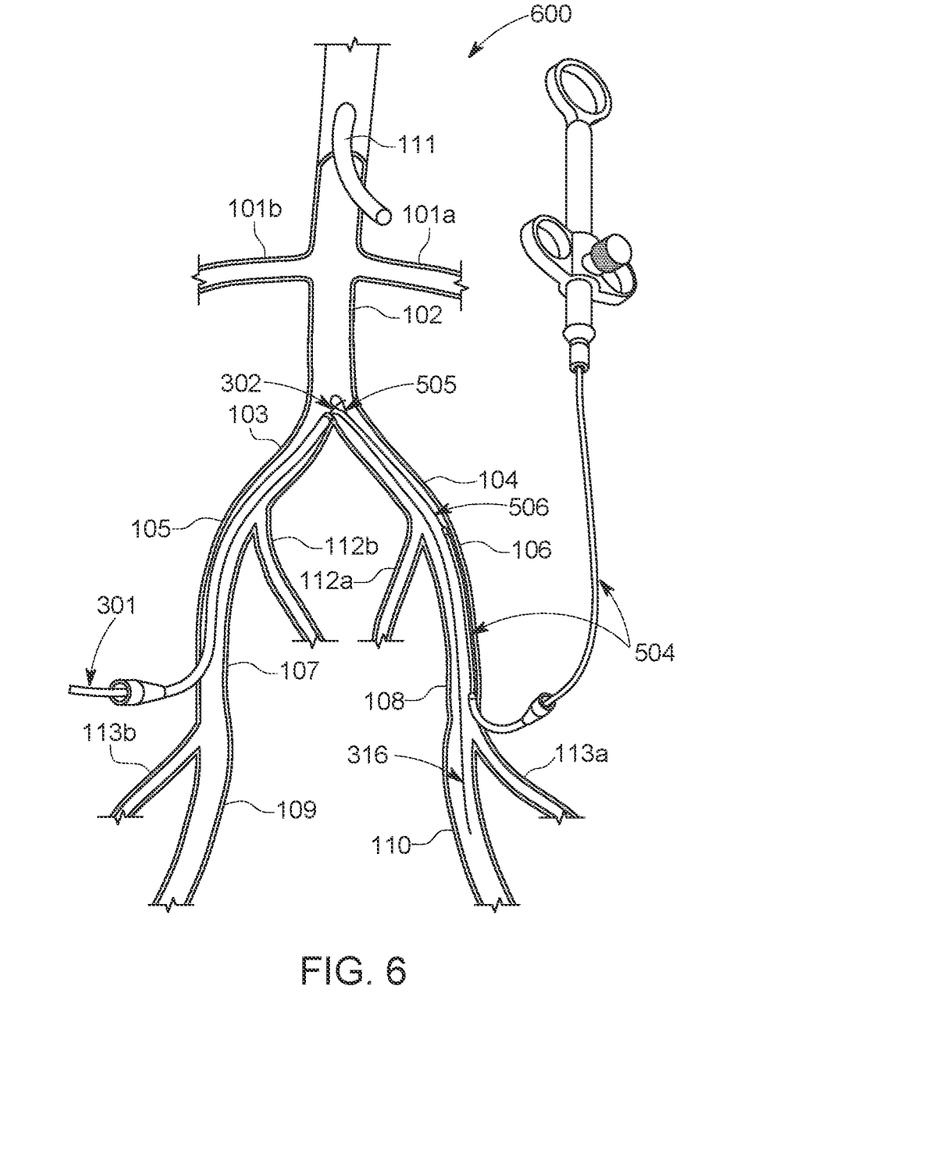
FIG. 6 illustrates a process of inserting the guide sheath of FIG. 3A through the main access sheath of FIG. 4 to the aortic bifurcation and snaring of the stabilization wire, in accordance with an embodiment of the disclosure.

FIG. 6 illustrates a process of inserting the guide sheath 300 (of FIG. 3A) through the main access sheath 401 (of FIG. 4), in accordance with an embodiment of the disclosure. The guide sheath 300 can include an integrated stabilization wire 302 exposed at or about the distal tip of the main access sheath 401. In some embodiments, the integrated stabilization wire 302 of guide sheath 300 is first introduced into main access sheath 401 with the aid of a guide wire introducer (not shown) and advanced alongside the pre-positioned main access guide wire 316 towards the aortic bifurcation 115. The tip of the integrated stabilization wire 302 can be finally positioned inside the snare loop 505. The stabilization wire 302 can then be captured and secured by the snare loop 505 by advancing the snare catheter 504 until the snare loop 505 collapses into the lumen of the snare catheter 504.

Figure 7:
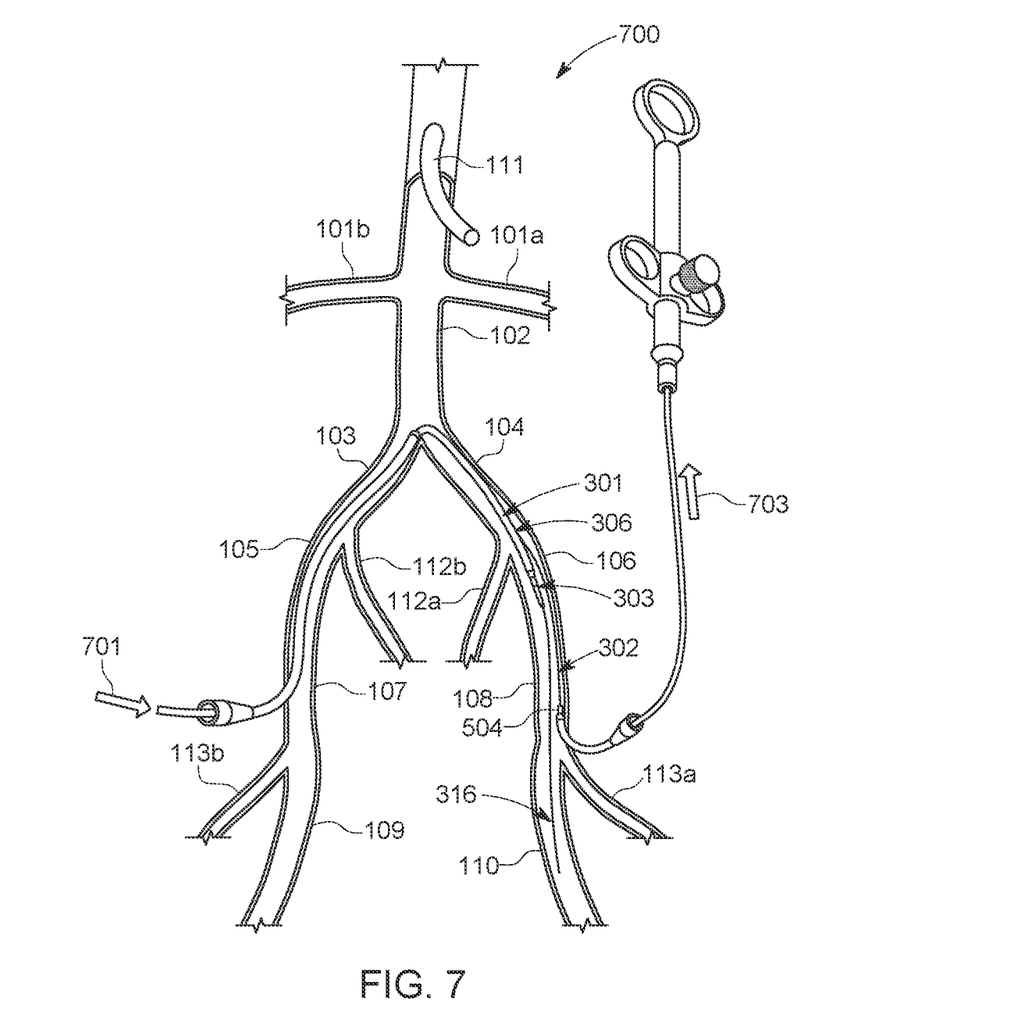
FIG. 7 illustrates a process of applying a pull force to the guide sheath of FIG. 3A into the ipsilateral iliac artery by retracting the snare device while providing a push force on the guide sheath from the contralateral side to externalize the stabilization wire, in accordance with an embodiment of the disclosure.

FIG. 7 illustrates a process of applying a pull force 703 to the guide sheath 300 by retracting the snare catheter 504 while providing a push force 701 on the guide sheath 300 (not labeled) from the contralateral side to externalize the stabilization wire 302. The pull force 703 can be applied to the distal end of the guide sheath 300 (not labeled). Of note, 301 which is the elongate member of the guide sheath is labeled. This pull force 703 is derived from the operator's retraction of the snare catheter 504 which has securely captured the stabilization wire 302. Simultaneously, a push force 701 can be applied to the proximal end of the guide sheath 300 (not labeled). These push and pull forces enable the guidance and ease placement of sheath 300 (not labeled), over the aortic bifurcation 115 and down the ipsilateral left iliac artery 104. The guide sheath 300 (not labeled) with the dilator 303 and the stabilization wire 302 can be guided to the left common femoral artery access site 404 (as shown in FIG. 4). The stabilization wire 302 can be externalized (i.e. out of the patient's body) [not shown] by retracting it through the low profile ipsilateral access sheath 403 (labeled previously in FIGS. 4 and 5). The stabilization wire 302 may be retracted (not shown in FIG. 7, but shown in FIG. 8) until the stabilization wire transition 306 is positioned at or about the distal tip of the low profile ipsilateral sheath 403.

Figure 8:
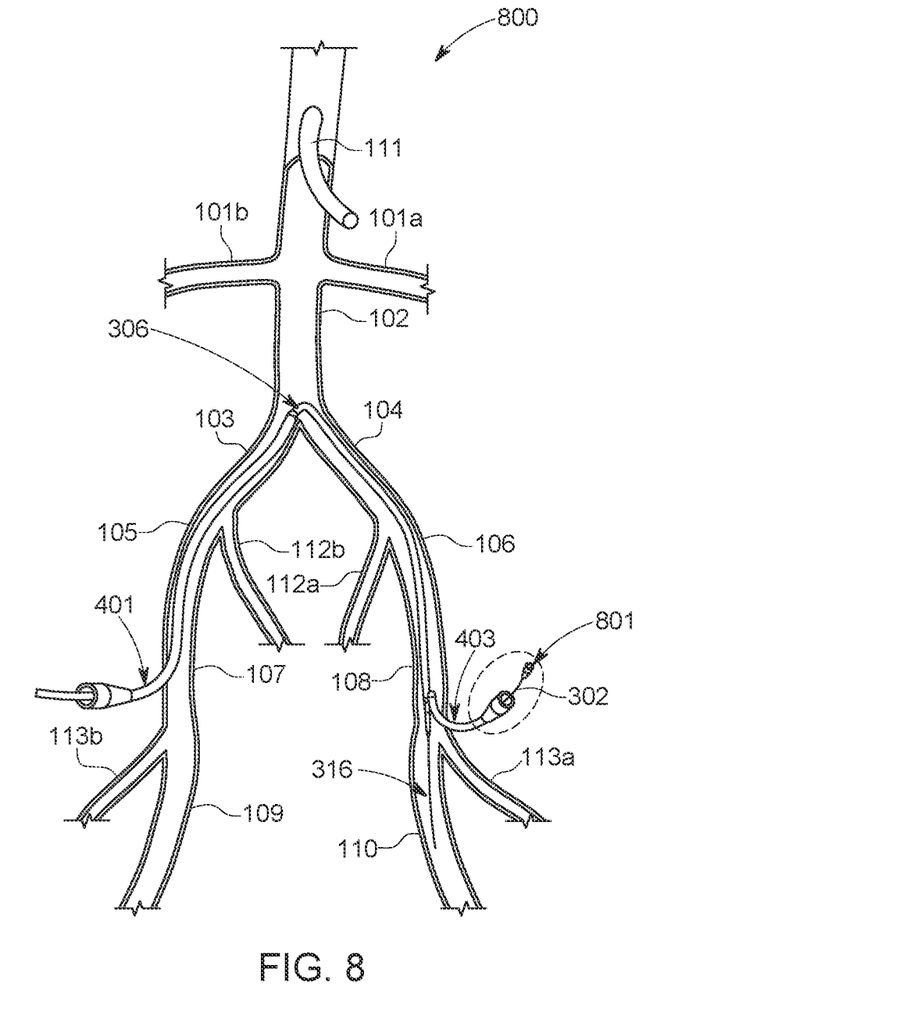
FIG. 8 illustrates a process of anchoring an externalized stabilization wire of the guide sheath of FIG. 3A to provide end-to-end stabilization for the procedural lumen, in accordance with an embodiment of the disclosure.

FIG. 8 illustrates a process of anchoring an externalized stabilization wire 302 of the guide sheath 300 (not labeled) to provide end-to-end stabilization for the procedural lumen. The stabilization wire 302 can be anchored in place by sliding a torque device 801 (or using any equivalent locking device) over the externalized portion of the stabilization wire 302. The stabilization wire 302 can then be tightened or otherwise locked or anchored at or about the hub of the low profile ipsilateral access sheath 403. By locking or anchoring the stabilization wire 302 outside the low profile ipsilateral access sheath 403, the guide sheath 300 (not labeled) is securely stabilized and tethered. In this way, the guide sheath 300 (not labeled) is prevented from backing up and/or prolapsing into the abdominal aorta 102 when advancing procedural catheters and other interventional devices through the main lumen of guide sheath 300 (not labeled). Ultimately, the anchored guide sheath 300 (not labeled) provides superior pushability of interventional devices, thereby allowing more distal access to the ipsilateral limb vessels and enabling crossing of tight lesions or even chronic total occlusions. Furthermore, this enhanced stability enables the use of stiffer devices (e.g. atherectomy catheters), which typically may elicit prolapse of a guide sheath that is not anchored.

Figure 9:
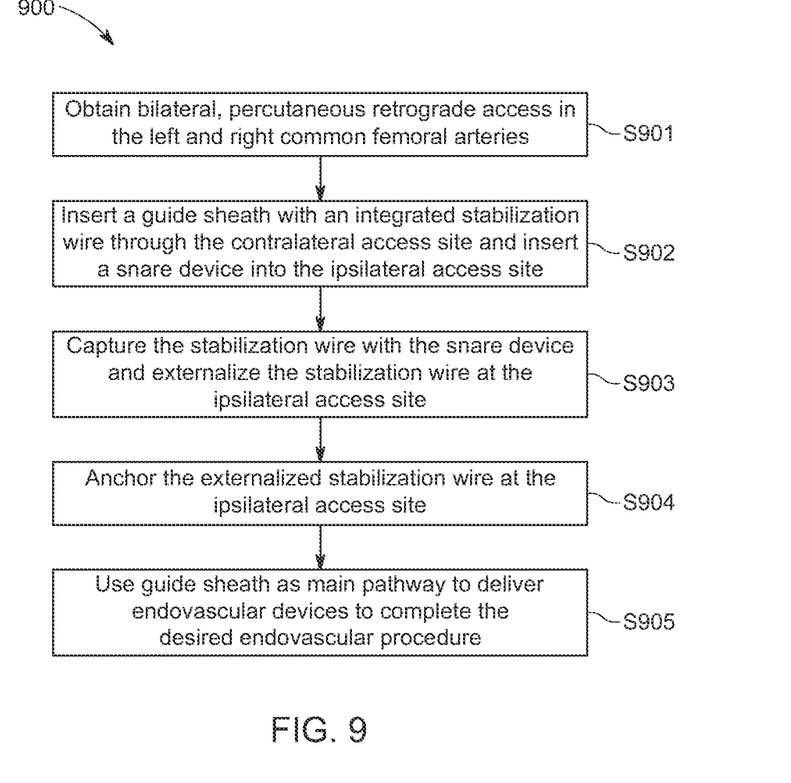
FIG. 9 illustrates a process flow diagram for accessing and stabilizing the guide sheath in lower limb interventions, in accordance with an exemplary embodiment of the disclosure.

FIG. 9 provides a flow chart diagram 900 for accessing and stabilizing the guide sheath 300 with an integrated stabilization wire 302 in lower limb interventions, indicated by general reference character 900. The process commences at step S901 where the bilateral, percutaneous retrograde access is obtained for the left and right common femoral arteries.

At step S902, a guide sheath is inserted with an integrated stabilization wire through the contralateral access site and the snare device is inserted into the ipsilateral access site. At step S903, the stabilization wire is captured with the snare device and the stabilization wire at the ipsilateral access site is externalized. At step S904, the externalized stabilization wire anchored at the ipsilateral access site. Finally, the process advances to S905, where the guide sheath is used as a main pathway to deliver endovascular devices to complete the desired endovascular procedure.

While the stabilization schemes proposed above describe a guide sheath with integrated stabilization wire that can provide stability in procedures conducted in tortuous branches of major peripheral vessels of the lower extremities, it is understood that it is not meant to be exhaustive. There may be other scenarios possible for access and stabilization of procedural catheter or sheath depending on the location of the procedure and the nature of the patient such as radial or brachial access. The preferred method will vary based on the location of the procedure and the nature of the patient.

The invention claimed is:

1. A sheath catheter for performing a lower extremity procedure comprising:
   a catheter body comprising a proximal end and a distal end, the catheter body comprising a lumen therein;
   a plurality of radio-opaque markers affixed to the catheter body;
   a stabilization wire partially integrated and attached to a wall of the catheter body within the lumen between the proximal and distal ends of the catheter body, the stabilization wire extending beyond the distal end of the catheter body, the stabilization wire having a flat cross section where the stabilization wire is attached to the wall of the catheter body within lumen and a circular cross section where the stabilization wire extends beyond the distal end of the catheter body;
   wherein the distal end of the catheter body and the stabilization wire configured to be inserted into a vasculature via a contralateral percutaneous access and guided within the vasculature using the plurality of radio-opaque markers;
   wherein the distal end of the stabilization wire is configured to exit the vasculature at an ipsilateral percutaneous access and is enabled to provide stability and support to a procedural catheter inserted into the vasculature via the sheath catheter.

2. The sheath catheter of claim 1, wherein a proximal end of sheath catheter is connected to a hub outside the contralateral percutaneous access,
   the hub enabled to fix the proximal end of the sheath catheter outside the contralateral percutaneous access.

3. The sheath catheter of claim 2, wherein the hub is configured to guide the sheath catheter within the vasculature and wherein the hub comprises a hemostasis valve.

4. The hub of claim 2, wherein the hub is configured to guide the sheath catheter within the vasculature and provide hemostasis at the contralateral percutaneous access.

5. The sheath catheter of claim 1, wherein the distal end of the stabilization wire is configured to be located outside the ipsilateral percutaneous access.

6. The sheath catheter of claim 1, wherein a proximal end of the sheath catheter is configured to be connected to a hub outside the contralateral percutaneous access and a distal end of the stabilization wire is configured to be locked outside the ipsilateral percutaneous access to enable a tension and stabilization force to be applied to the sheath catheter.

7. The sheath catheter of claim 6, wherein application of tension and stabilization to the sheath catheter comprises application of a tension and stabilization force between the proximal end and distal end of the sheath catheter.

8. The sheath catheter of claim 6, wherein the sheath catheter is configured to allow a plurality of guide wires and procedural catheters to be delivered to the vasculature via the lumen of the catheter body.

9. The sheath catheter of claim 8, wherein the tension and stabilization force enables the plurality of guide wires and procedural catheters to be stabilized during access and procedures.

10. A system for performing a procedure within a lower extremity vasculature comprising:
    a sheath catheter comprising a catheter body having a proximal end and a distal end, the catheter body comprising a lumen therein extending from the proximal end to the distal end of the catheter body;
    a plurality of radio opaque markers affixed to the catheter body, the plurality of radio opaque markers configured to allow for guidance and determination of the location of the catheter body within the vasculature during access;
    a stabilization wire having a proximal end and a distal end, the stabilization wire partially embedded in and attached to an internal wall of the lumen of the catheter body between the proximal and distal ends of the catheter body, the stabilization wire extending beyond the distal end of the catheter body forming a distal end of the sheath catheter, the stabilization wire having a flat shape with a rectangular cross section within the catheter body and a round cross section outside the distal end of the catheter body;
    the distal end of the catheter body configured to access the vasculature via a contralateral percutaneous access;
    the proximal end of the catheter body comprising a hub enabled to guide the sheath catheter, the hub comprising a hemostasis valve, wherein the hub is configured to be outside the contralateral percutaneous access;
    a snare catheter configured to deliver a snare device with a snare loop;
    wherein the snare catheter is configured to access the vasculature via an ipsilateral percutaneous access enabling the snare loop to capture and externalize the stabilization wire at the ipsilateral percutaneous access; and
    wherein the externalized distal end of the stabilization wire is configured to be locked outside the ipsilateral percutaneous access by a lock mechanism.

11. The system of claim 10, wherein having the proximal end of the sheath catheter outside the contralateral percutaneous access and the distal end of the sheath catheter outside the ipsilateral percutaneous access enable application of a tension and stabilization force to the sheath catheter.

12. The system of claim 10, wherein at least one of the plurality of radio opaque markers are affixed at the distal end of the catheter body.

13. The system of claim 10, wherein the lumen within the catheter body is configured to allow a plurality of guide wires and procedural catheters to be delivered to the vasculature.

14. The system of claim 11, wherein the application of the tension and stabilization force enable stabilization of the sheath catheter and the plurality of guide wires and procedural catheters during access to a site of the procedure and during the procedure.

15. The system of claim 10, wherein the snare device comprises a snare wire.

16. The system of claim 10, wherein the hub comprises a side port.

17. The system of claim 16, wherein the side port comprises a stopcock with a luer connector.

18. The system of claim 17, wherein the hemostasis valve comprises a touhy borst valve or a duck-bill valve.

19. The system of claim 10, wherein the lock comprises a torque device.

20. The system of claim 10, wherein having both the proximal and distal ends of the sheath catheter accessible outside the vasculature enable a push-pull action to be used during guidance of the sheath catheter within the vasculature.

21. The system of claim 20, wherein the push-pull action enables easier access for the distal end of the catheter body to a location close to the location of the procedure, enabling easy access for the procedure catheters to a location of the procedure.

\* \* \* \* \*